US012508381B2

(12) United States Patent
Mieskoski

(10) Patent No.: US 12,508,381 B2
(45) Date of Patent: Dec. 30, 2025

(54) APPARATUS AND METHOD FOR AN ENDOTRACHEAL TUBE HOLDER

(71) Applicant: Darlene Mieskoski, Strongsville, OH (US)

(72) Inventor: Darlene Mieskoski, Strongsville, OH (US)

(*) Notice: Subject to any disclaimer, the term of this patent is extended or adjusted under 35 U.S.C. 154(b) by 988 days.

(21) Appl. No.: 17/675,068

(22) Filed: Feb. 18, 2022

(65) Prior Publication Data

US 2022/0288337 A1 Sep. 15, 2022

Related U.S. Application Data

(60) Provisional application No. 63/161,026, filed on Mar. 15, 2021.

(51) Int. Cl.
*A61M 16/04* (2006.01)

(52) U.S. Cl.
CPC ............................... *A61M 16/0497* (2013.01)

(58) Field of Classification Search
CPC ................................................ A61M 16/0497
See application file for complete search history.

(56) References Cited

U.S. PATENT DOCUMENTS 2,353,643 A * 7/1944 Bulbulian ............ A62B 18/084 2/9
4,191,180 A * 3/1980 Colley .................. A61M 25/02 128/DIG. 26
4,744,358 A * 5/1988 McGinnis ......... A61M 16/0497 128/DIG. 26
5,345,931 A * 9/1994 Battaglia, Jr. ......... A61M 25/02 604/179
5,996,581 A * 12/1999 Duch ................ A61M 16/0497 128/206.26
6,840,238 B1 * 1/2005 Van Hegelsom . A61M 16/0488 128/207.14
6,889,689 B1 * 5/2005 Neuman ........... A61M 16/0683 128/207.18
7,568,484 B2 * 8/2009 Bierman ........... A61M 16/0497 128/206.27
2007/0119454 A1 * 5/2007 Berthon-Jones ............................ A61M 16/0683 128/204.23
2014/0261463 A1 * 9/2014 Visconti ............. A61B 1/00154 128/861
2014/0373278 A1 * 12/2014 Scott ..................... A61F 5/3707 5/640
2017/0197049 A1 * 7/2017 Doll .................. A61M 16/0497
2019/0358421 A1 * 11/2019 Landis ................ A61M 5/1418

* cited by examiner

*Primary Examiner* — Joseph D. Boecker
*Assistant Examiner* — Thomas W Greig

(57) ABSTRACT

Provided is an endotracheal tube holder comprising a harness adapted to be engaged with an associated patient's head, the harness having a top, bottom, front, back, first side, and second side; an adjustable transverse band; an adjustable coronal band; a first strap elongated to define a first end engaged with the transverse band on the first side and a second end; a second strap elongated to define a first end engaged with the transverse band on the second side and a second; a set of pads having a first pad engaged to the first strap, and a second pad engaged to the second strap; and a platform having an elongated rail extending between the first pad and the second pad, a slide engaged with the rail, and a tube cradle on top of the slide, the tube cradle being adapted to engage and hold an endotracheal tube.

8 Claims, 10 Drawing Sheets

APPARATUS AND METHOD FOR AN ENDOTRACHEAL TUBE HOLDER

CROSS-REFERENCE TO RELATED APPLICATIONS

This patent application claims the benefit of U.S. Prov. Ser. No. 63/161,026 filed Mar. 15, 2021. The latter application is incorporated by reference herein.

BACKGROUND

The present subject matter relates to medical equipment and particularly to an endotracheal tube (ETT). More specifically, the present subject matter relates to an apparatus and method for holding an endotracheal tube (ETT) in place during use.

An ETT tube is a tube adapted to be inserted into an associated patient's mouth, then advanced through the associated patient's trachea, and then further into the lungs. The ETT is typically used when the associated patient is no longer able to breath on his own. This ETT provides airway stabilization to allow oxygen and mechanical support via a breathing machine such as a mechanical ventilator.

Unscheduled removal of the ETT is undesirable. Unscheduled removal of an ETT can include accidental removal or removal by an untrained agent. Unscheduled removal may include, without limitation the associated patient intentionally pulling the ETT tube out of his person (extubation). Unscheduled removal may also occur due to mechanical forces on the ETT resulting from lifting a patient in bed, rolling a patient from side to side, transporting for a procedure, and moving from a bed to bed or bed to table.

Unscheduled removal of the ETT can result in one or more adverse events including but not limited to airway trauma, longer ventilatory support duration, longer hospital stays, increased medical costs and health risks, or combinations thereof.

In order to prevent unscheduled removal of an ETT, the ETT may be used in conjunction with an ETT holder but the existing ETT holders have problems. For example, existing ETT holders are not well-adapted to the prevention of jaw fatigue from holding the mouth open for a long period of time. Existing ETT holders also are not well adapted for proper stabilizing, anchoring, position adjustment and securing. These existing ETT devices are not well adapted to counter balances external loads, forces torque, twisting, pulling, rotating, lifting and moving. Some existing ETT holders use straps that tend to stretch out or slip off the head, or use clamps from a plastic frame that can squeeze a ETT tub causing narrowing, or use adhesive pads which can cause skin tearing, or use tape which doesn't let air to the skin or can breakdown, deteriorate, create ulcers, or use ties which can loosen or become soiled with oral bodily fluids.

It remains desirable to develop an improved ETT holder which overcomes some of all of the above problems

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

Accordingly, the present subject matter is directed to an apparatus and method for an endotracheal tube holder that substantially obviates one or more problems resulting from the limitations and deficiencies of the related art.

In accordance with one non-limiting embodiment of the present invention, there is provided an endotracheal tube holder comprising a harness adapted to be engaged with an associated patient's head; the harness having a top, bottom, front, back, first side, and second side; an adjustable transverse band; an adjustable coronal band; a first strap elongated to define a first end engaged with the transverse band on the first side and a second end; a second strap elongated to define a first end engaged with the transverse band on the second side and a second; a set of pads having a first pad engaged to the first strap, and a second pad engaged to the second strap; and a platform having an elongated rail extending between the first pad and the second pad, a slide engaged with the rail, and a tube cradle on top of the slide, the tube cradle being adapted to engage and hold an endotracheal tube.

In accordance with one non-limiting embodiment of the present invention, there is provided a method of using an endotracheal tube holder comprising providing an endotracheal tube; providing an associated patient having a head, the head having a top, a front having a mouth, a first cheek, a second cheek, and a chin, a back opposite the front with respect to a coronal plane, a first side, and a second side opposite the first side with respect to a sagittal plane and a transverse plane mutually orthogonal to both the coronal plane and the sagittal plane; providing an endotracheal tube holder having a flexible and moldable harness adapted to be operatively engaged with the head, the harness having an adjustable transverse band extending in the transverse plane from the front to the back and adapted to be selectably secured around the head; an adjustable coronal band extending in the coronal plane from the first side to the second side and adapted to be selectably secured over the head; a first strap elongated to define a first end of the first strap and a second end of the first strap opposite the first end of the first strap, the first end of the first strap being engaged with the transverse band on the first side; a second strap elongated to define a first end of the second strap and a second end of the second strap opposite the first end of the second strap, the first end of the second strap being engaged with the transverse band on the second side; a set of pads having a first securing pad engaged to the first strap, and a second securing pad engaged to the second strap; and a platform having an elongated rail operationally engaged with and extending between the first securing pad and the second securing pad, a slide operationally and slidably engaged with the rail, and a tube cradle on top of and operationally engaged with the slide, the tube cradle being adapted to selectably engage and hold fast the endotracheal tube; inserting the endotracheal tube into the mouth of the patient; operatively engaging the harness with the head; securing the transverse band around the head; securing the coronal band over the head; and engaging the endotracheal tube with the tube cradle.

It is to be understood that the foregoing general description and the following detailed description of the present subject matter are merely exemplary and explanatory in nature. As such, the foregoing general description and the following detailed description should not be construed to limit the scope of the appended claims in any sense.

BRIEF DESCRIPTION OF THE DRAWINGS

Various exemplary embodiments of the present subject matter will be described in detail, wherein like reference numerals refer to identical or similar components, with reference to the following figures, wherein.

Throughout the figures, unless otherwise noted, the same parts are denoted using the same reference characters so that, as a general rule, they will only be described once.

DETAILED DESCRIPTION

Figure 1:
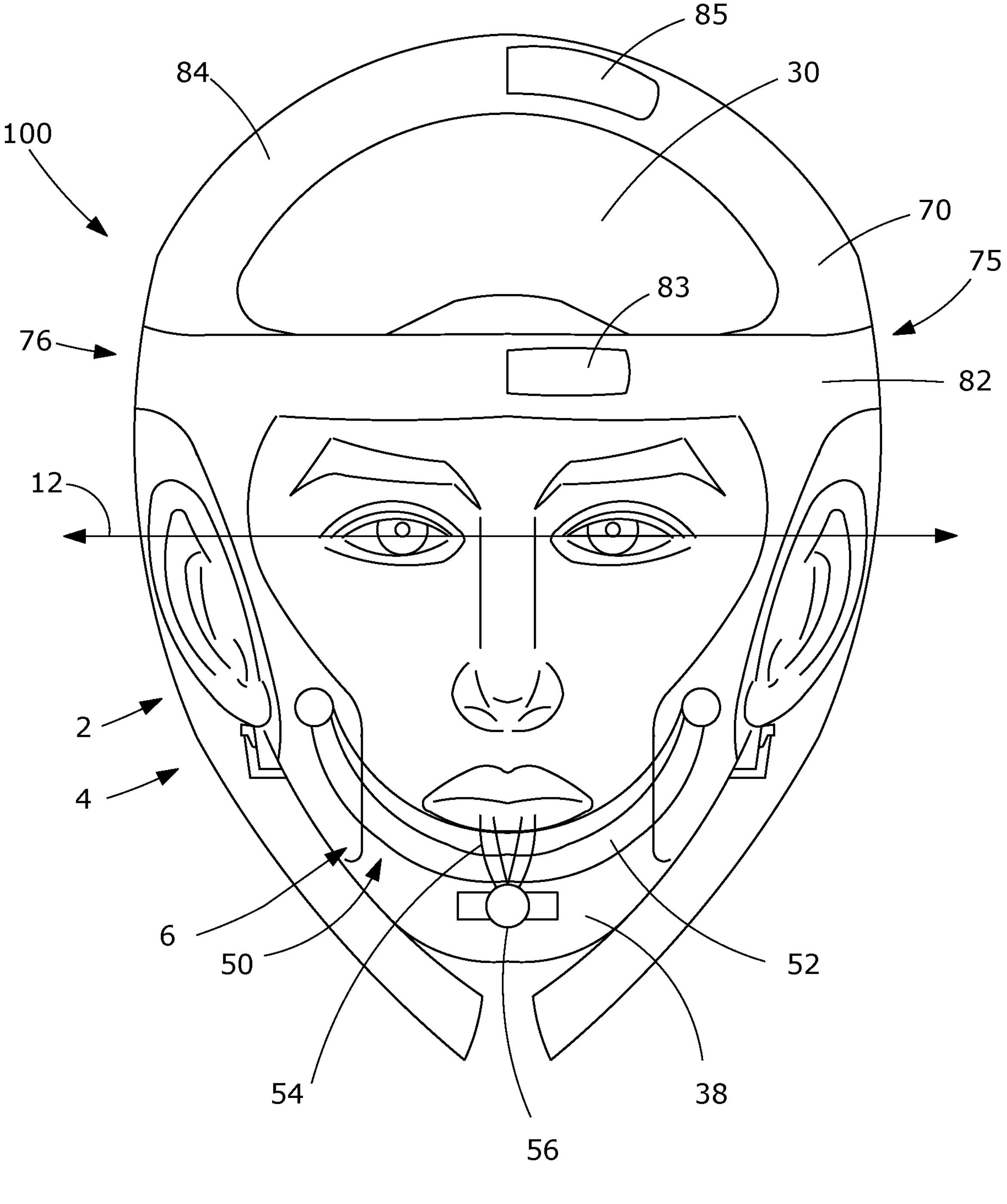
FIG. 1 is a front view of an endotracheal tube holder engaged to an associated patient, according to a first embodiment thereof.

The claimed subject matter is now described with reference to the drawings. In the following description, for purposes of explanation, numerous specific details are set forth in order to provide a thorough understanding of the claimed subject matter. It may be evident, however, that the claimed subject matter may be practiced with or without any combination of these specific details, without departing from the spirit and scope of this invention and the claims.

An illustrative first embodiment of an endotracheal tube holder 100 is seen generally in FIGS. 1-8. The endotracheal tube holder 100 generally comprises a harness 70, pads 40, a platform 50, and, optionally, a cap 30. The embodiments herein may be described generally with respect to an associated patient 2, body parts of the associated patient 2, such as, and without limitation, an associated head 4, and the imaginary anatomical planes commonly used in anatomical descriptions. These latter imaginary anatomical planes are the mutually orthogonal sagittal, coronal, and transverse planes. The sagittal plane 16 divides the associated head 4 into a left section and a right section. The coronal plane divides 14 the associated head 4 into a front section and back section. The transverse plane 12 divides the associated head 4 into a top section and a bottom section.

Referring now to FIGS. 1, 3, 4, 7, and 8 particularly, the harness 70 may be flexible and moldable and be adapted to operatively engage with an associated head 4 of an associated patient 2. The harness may have a top 71, a bottom 72 opposite the top 71 with respect to a transverse plane 12, a front 73, a back 74 opposite the front 73 with respect to a coronal plane 14, a first side 75, and a second side 76 opposite the first side 75 with respect to a sagittal plane 16.

The harness 70 may have an adjustable transverse band 82 extending in the transverse plane 12 from the front 73 to the back 74 and adapted to be selectably secured around the associated head 4. The transverse band 82 may be formed from any material chosen with good engineering judgment and may be fastened in any manner chosen with good engineering judgment. In some embodiments, the transverse band 82 comprises a cotton fabric, a polyester fabric, nylon fabric, or combinations thereof. In some embodiments the transverse band 82 is fastened with a transverse band fastener 83 such as, and without limitation, a buckle, or a hook and loop fastener, or other fastener chosen with good engineering judgment.

The harness 70 may have an adjustable coronal band 84 extending in the coronal plane 14 from the first side 75 to the second side 76 and adapted to be selectably secured over the associated head 4. The coronal band 84 may be formed from any material chosen with good engineering judgment and may be fastened in any manner chosen with good engineering judgment. In some embodiments, the coronal band 84 comprises a cotton fabric, a polyester fabric, nylon fabric, or combinations thereof. In some embodiments the coronal band 84 is fastened with a coronal band fastener 85 such as, and without limitation, a buckle, or a hook and loop fastener, or other fastener chosen with good engineering judgment.

The harness 70 may have a first strap 86 elongated to define a first end 86A of the first strap and a second end 868 of the first strap opposite the first end of the first strap, the first end 86A of the first strap being engaged with the transverse band 82 on the first side 75. In some embodiments, the first strap 86 is formed of the same material as the transverse band 82, but this is not limiting. In other acceptable embodiments, the first strap 86 is formed of a different material from that of which the transverse band 82 is formed.

The harness 70 may have a second strap 88 elongated to define a first end 88A of the second strap and a second end 88B of the second strap opposite the first end of the second strap, the first end 88A of the second strap being engaged with the transverse band 82 on the second side 76. In some embodiments, the second strap 88 is formed of the same material as the transverse band 82, but this is not limiting. In other acceptable embodiments, the second strap 88 is formed of a different material from that of which the transverse band 82 is formed.

In some embodiments the harness 70 is designed to have sufficient strength to hold the pads 40 and platform 50 in place once an associated endotracheal tube is engaged thereto, even during movements, turning, or the like, without substantial discomfort or chaffing. As used herein this latter sufficient strength is sufficient to provide a holding force sufficient to hold an associated endotracheal tube in place during ordinary patient motion and rotations. In some embodiments, substantial discomfort or chaffing are avoided, prevented, minimized, or reduced by careful selection of materials of and by careful choice of the area over which the harness 70 spreads the forces applied over the head 4. A larger area may reduce pressure and may reduce discomfort or chaffing from pressure. In some embodiments the harness 70 is of sufficient area to distribute the above referenced holding force over the associated head 4 of the associated patient 2 without harm or discomfort to the patient 2.

The pads 40 may comprise a first securing pad 43 and a second securing pad 47. The first securing pad 43 may be engaged to the first strap 86 and may be engaged at a position on the first strap 86 proximate to the second end 86B of the first strap 86. The manner of engagement of the first securing pad 43 to the first strap 86 may be by any means chosen with good engineering judgment, but in some non-limiting embodiments is by releasable mechanical fasteners such as snaps, clips, quarter-turn fasteners, hook and loop fasteners, or the like. The second securing pad 47 may be engaged to the second strap 88 and may be engaged at a position on the second strap 88 proximate to the second end 88B of the second strap 88. The manner of engagement of the second securing pad 47 to the second strap 88 may be by any means chosen with good engineering judgment, but in some non-limiting embodiments is by releasable mechanical fasteners such as snaps, clips, quarter-turn fasteners, hook and loop fasteners, or the like. In some embodiments, substantial discomfort or chaffing are avoided, prevented, minimized, or reduced by careful selection of materials of and by careful choice of the area over which the pads 40 spread the forces applied over the head 4. A larger area may reduce pressure and may reduce discomfort or chaffing from pressure. In some embodiments, either the first securing pad 43 or the second securing pad 47 or both pads further comprises a cushion adapted to protect the associated head 4 of the associated patient 2. In some embodiments, either the first securing pad 43 or the second securing pad 47 or both pads further comprises a band opening adapted to receive a band such as a flexible elastic band, tape or similar material.

The platform 50 may have an elongated rail 52 operationally engaged with and extending between the first securing pad 43 and the second securing pad 47. The elongated rail 52 defines a guide path 53 extending at least part way between the first securing pad 43 and the second securing pad 47. The platform 50 may have a slide 54 operationally and slidably engaged with the elongated rail 52 such that the slide 54 may slide along guide path 53 and occupy any of a plurality of positions along guide path 53. In some non-limiting embodiments, elongated rail 52 is an elongated curved or straight beam with a path of elongation 53A that coincides with and thereby defines the guide path 53. In some non-limiting embodiments, elongated rail 52 is an elongated curved or straight beam with a substantially H-shaped cross-section wherein the slide fits over one of the uprights defined by the H-shaped beam allowing it to slide therealong. It is to be understood that an H-shaped cross-section is merely one acceptable form and that there are many other acceptable cross-section forms such as, and without limitation square, elliptical, rectangular, triangular, T-shaped, V-shaped, D-shaped, I-shaped, L-shaped, S-shaped, or otherwise as chosen with good engineering judgment. The elongated rail 52 may have one or more teeth 55 or other engagement elements thereon with which the slide 54 may be selectable engaged in order to hold the slide 54 fixed in an associated location with respect to the elongated rail 52. In some embodiment, the slide 54 may comprise one or more levers 56 which may be selectably adjusted to provide selectable engagement between the slide 54 and the teeth 55. It is to be understood that a lever is merely one acceptable component to provide selectable engagement between the slide 54 and the teeth 55 and that there are many other acceptable components which may be used to provide selectable engagement between the slide 54 and the teeth 55 such as, and without limitation, a pinion or screw. In embodiments in which the component used to provide selectable engagement between the slide 54 and the teeth 55 is a pinion or screw the teeth 55 may be operational engageable gear teeth, such as, and without limitation involute gear teeth. A screw paired with operationally engagable teeth 55 that are involute gear teeth may be of interest as a screw and gear teeth may be designed to be inherently locking and may provide a mechanical advantage.

The platform 50 may have a tube cradle 57 on top of and operationally engaged with the slide 54. The tube cradle 57 is adapted to selectably engage and hold fast an associated endotracheal tube. In the non limiting embodiment shown in FIG. 5A and FIG. 5C, and FIG. 5D the tube cradle 57 has a receiver 57A and a capture element 57B. The receiver 57A and the capture element 57B are adapted to operationally engage with one another to form a cylindrical cavity 58 adapted to capture and hold fast an associated endotracheal tube. In the non-limiting embodiment shown the capture element 57B is a flexible tab with an adhesive layer 57C that aids in capturing and holding fast an associated endotracheal tube. The flexible tab may be held in place by a latch, a mechanical fastener, such the interlocking tabs common to cable ties, zip ties, and similar fasteners, or other means chosen with good engineering judgment.

With reference now to FIGS. 6A-6D, in some embodiments the endotracheal tube holder 100 may comprise a bite protector 62 which shrouds the associated endotracheal tube to shroud it. The bite protector 62 may be installed over and around the associated endotracheal tube and may reinforce it to reduce or eliminate harm to the associated endotracheal tube by crushing or biting it. In some embodiments the tube cradle 57 is adapted to hold a bite protector 62 in place around the associated endotracheal tube.

Figure 2:
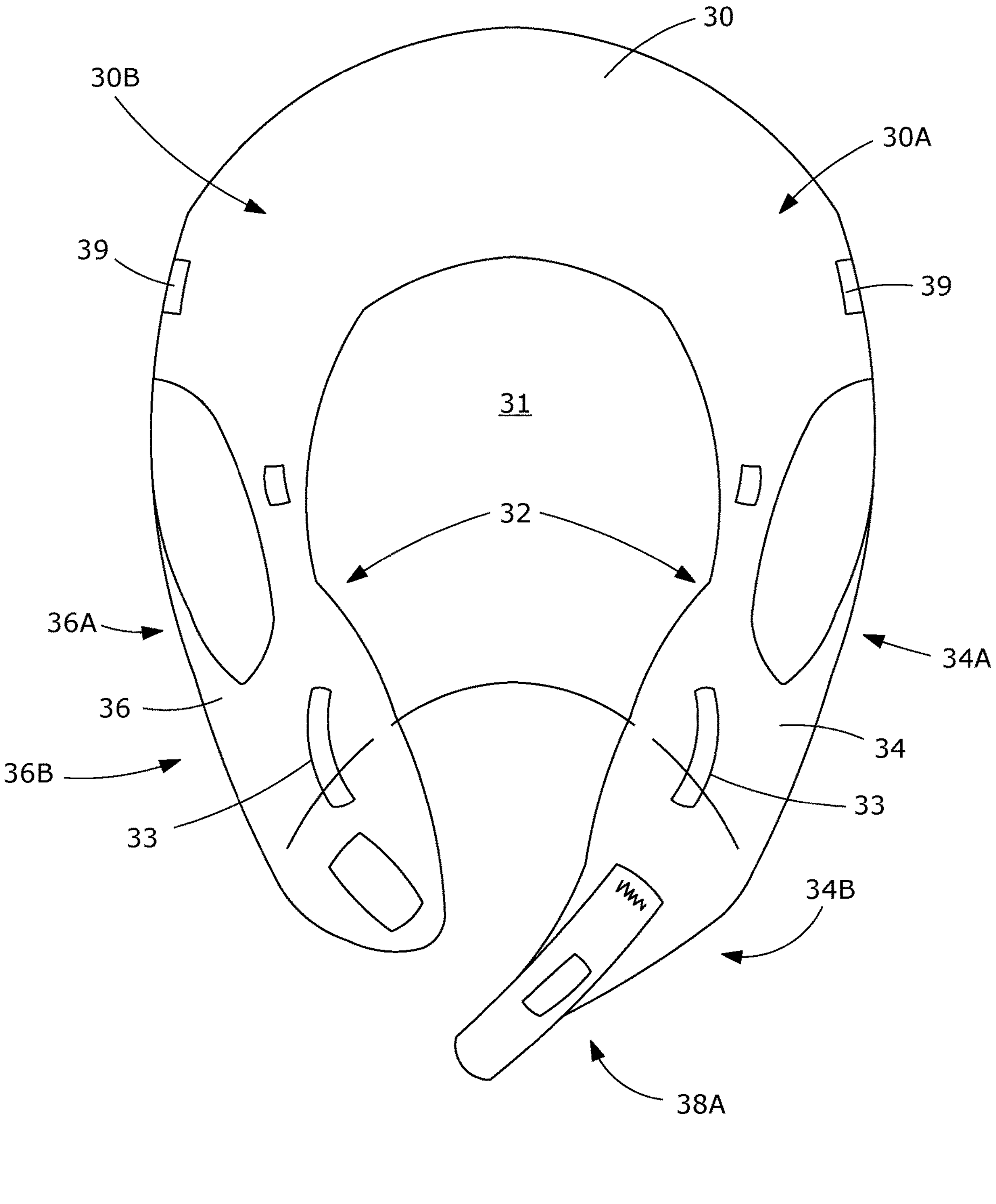
FIG. 2 is a front view of the cap from the first embodiment of the endotracheal tube holder of FIG. 1.
Figure 3:
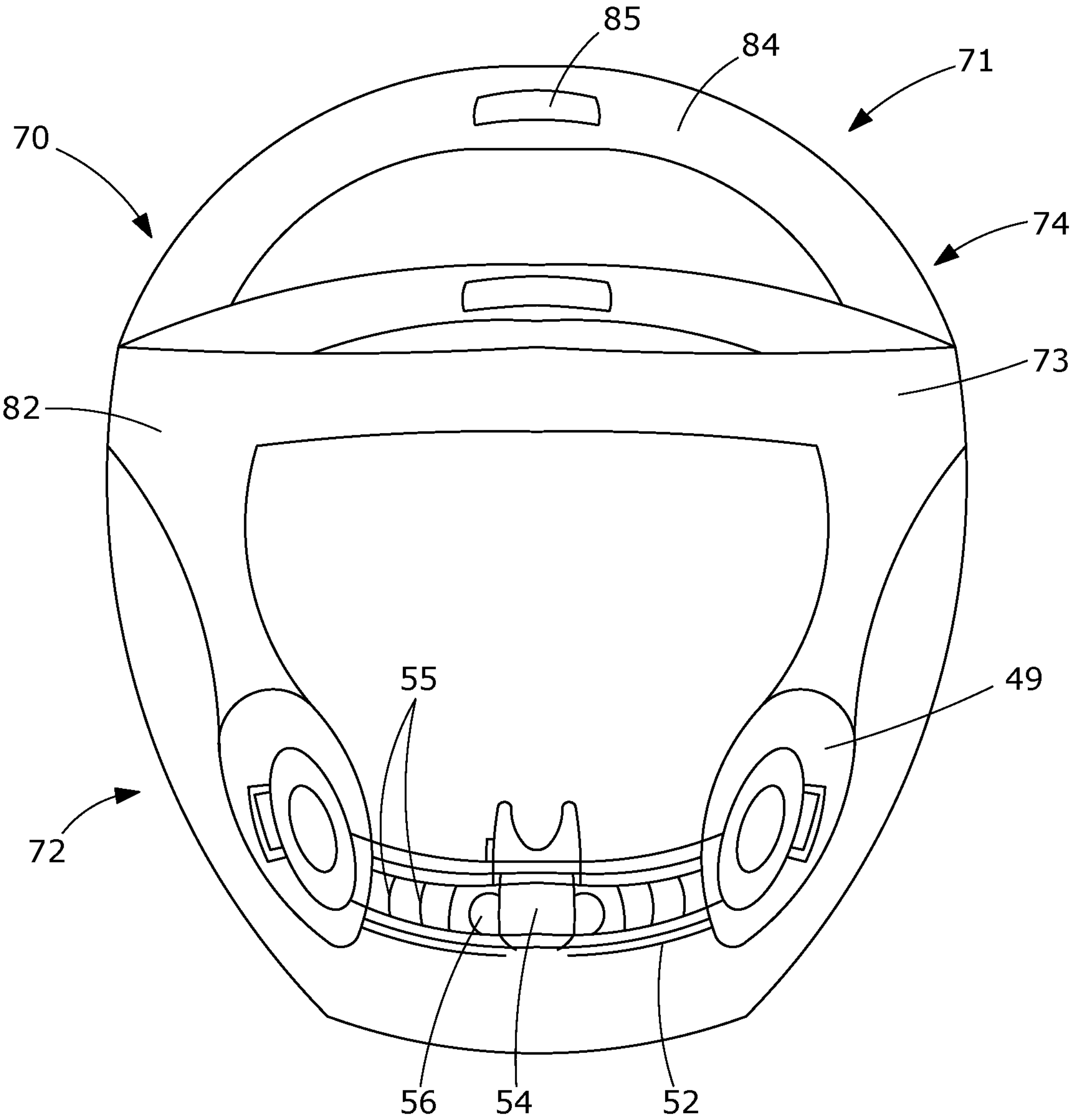
FIG. 3 is a front view of the harness with pads and platform operationally engaged therewith from the first embodiment of the endotracheal tube holder of FIG. 1.
Figure 4:
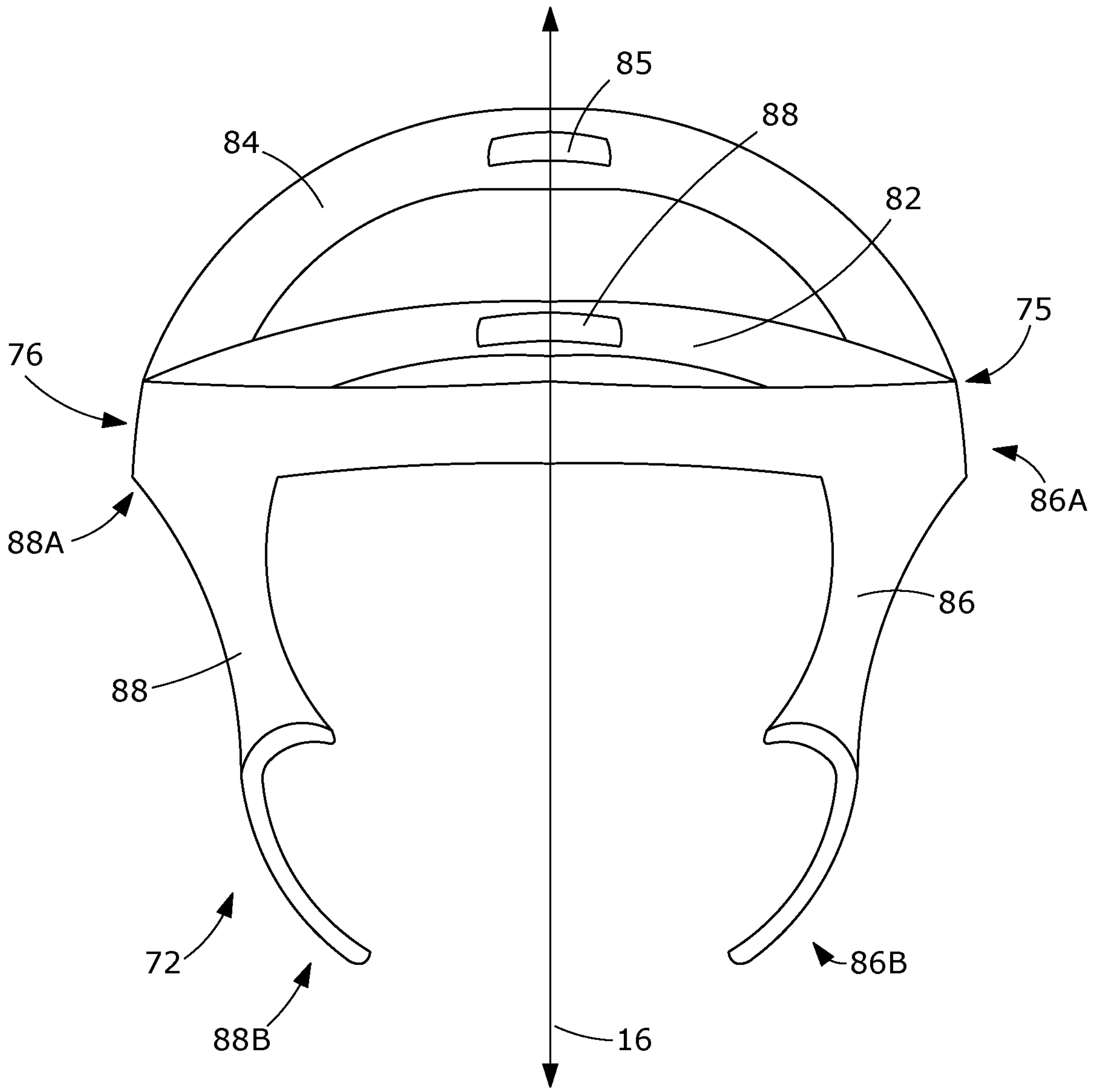
FIG. 4 is a front view of the harness from the first embodiment of the endotracheal tube holder of FIG. 1.
Figure 5A:
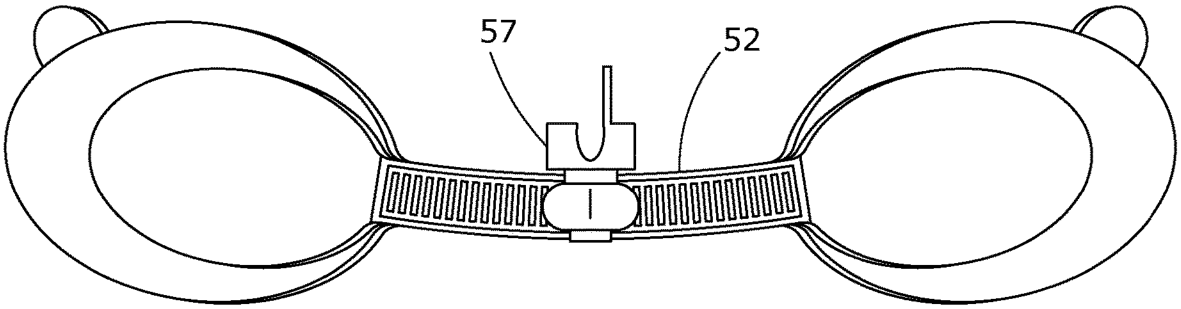
FIG. 5A is a front view of the pads and platform from the first embodiment of the endotracheal tube holder of FIG. 1.
Figure 5B:
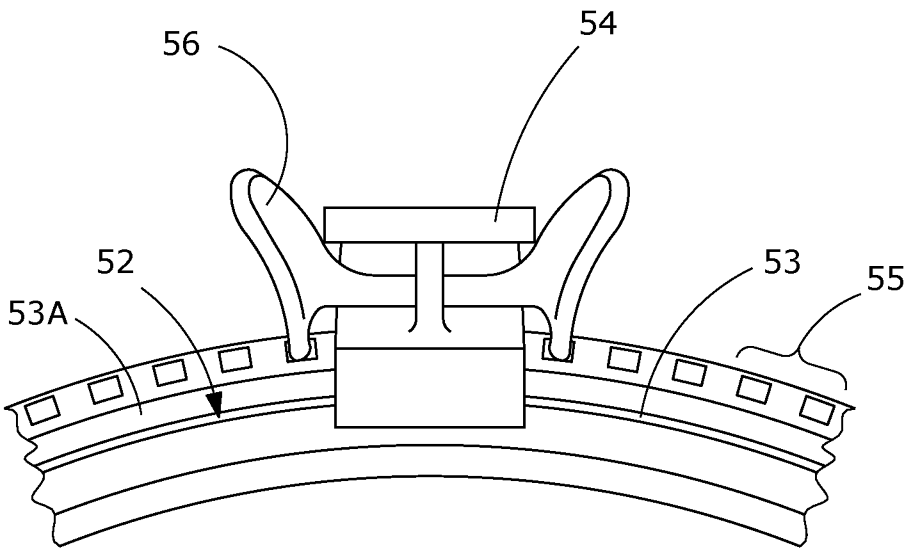
FIG. 5B is a top view of the platform from the first embodiment of the endotracheal tube holder of FIG. 1.
Figure 5C:
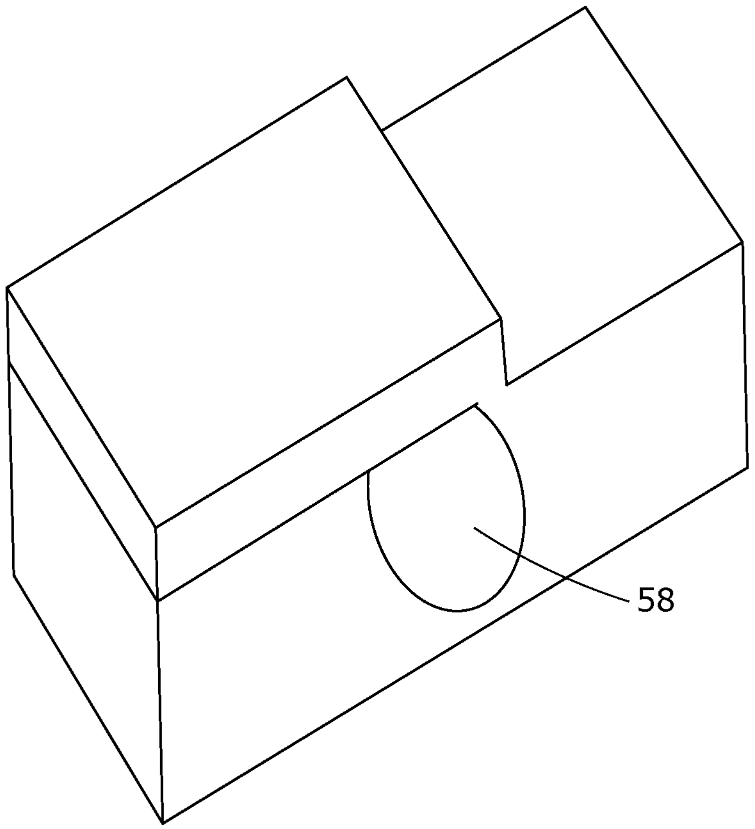
FIG. 5C is a perspective view of one embodiment of a tube holder from the first embodiment of the endotracheal tube holder of FIG. 1.
Figure 5D:
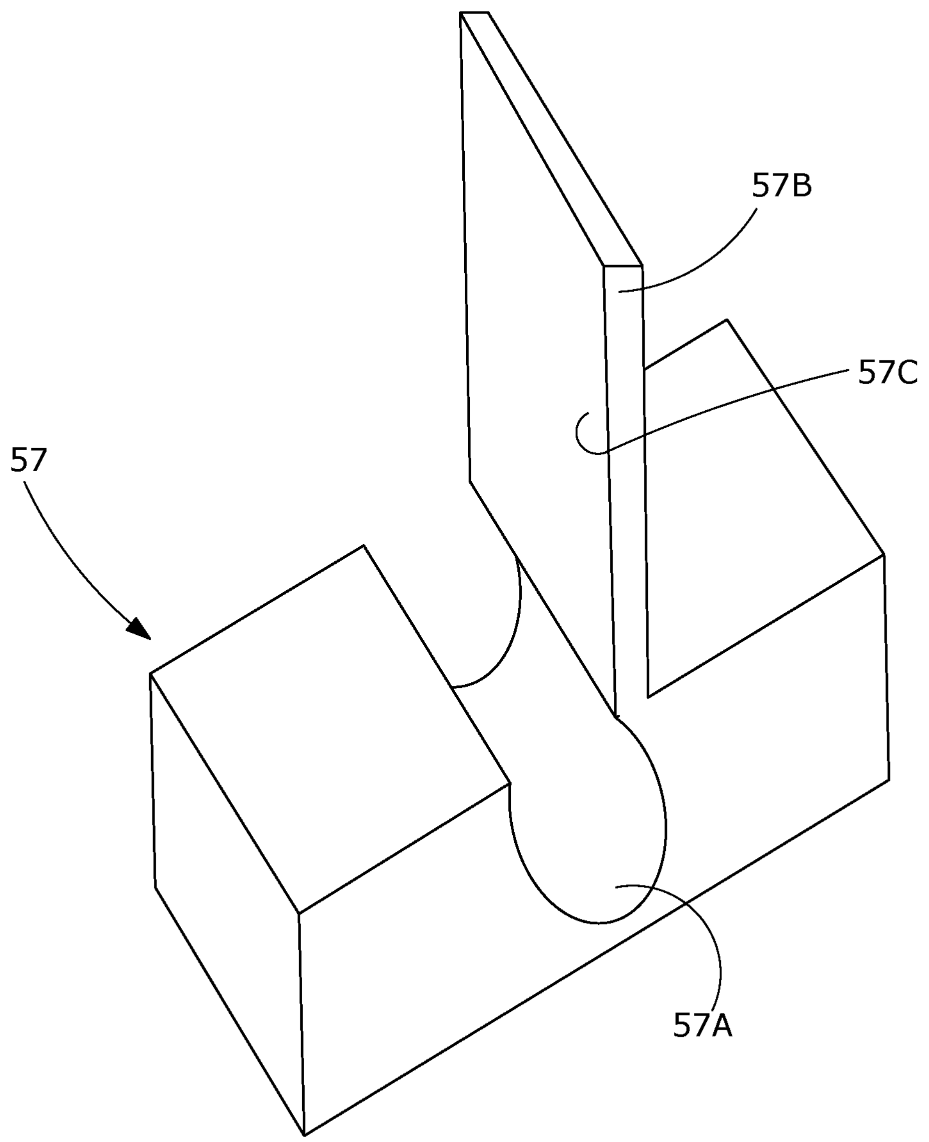
FIG. 5D is a perspective view of one embodiment of a tube holder from the first embodiment of the endotracheal tube holder of FIG. 1.
Figure 6:
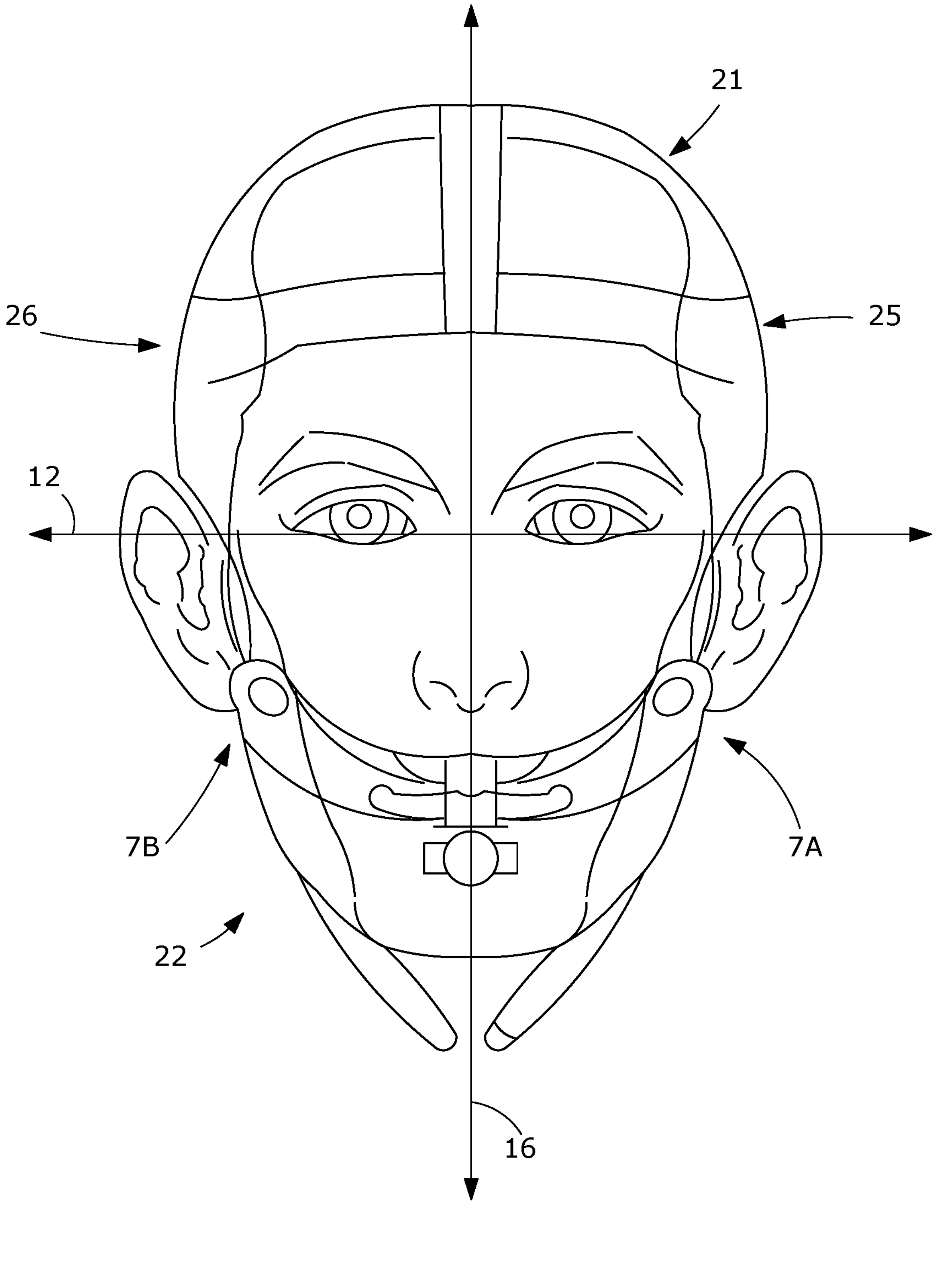
FIG. 6 is a front view of an endotracheal tube holder engaged to an associated patient, according to a second embodiment thereof.
Figure 7:
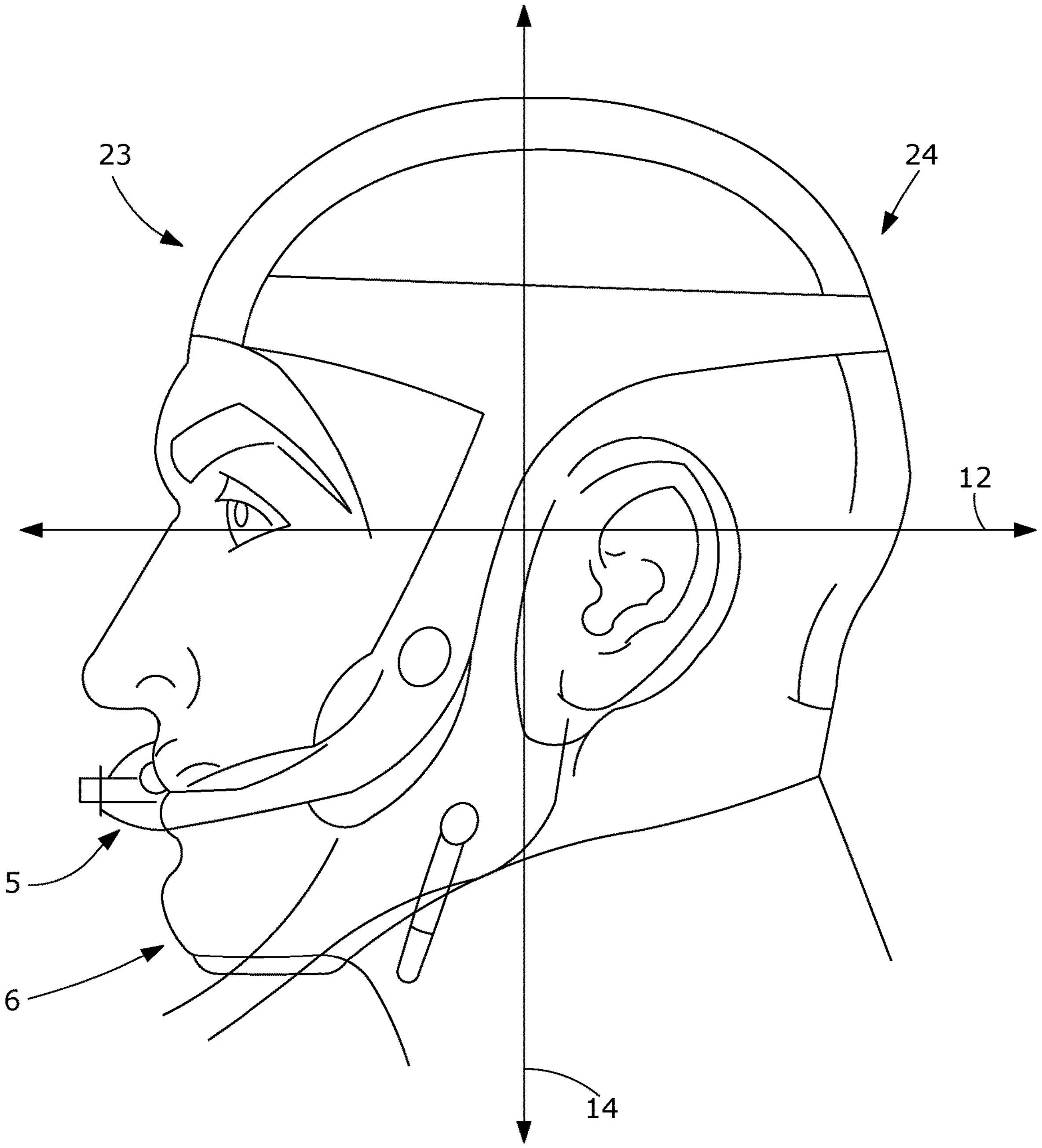
FIG. 7 is a side view of an endotracheal tube holder according to the second embodiment thereof shown in FIG. 6.

Referring now to FIGS. 1 and 2, the endotracheal tube holder 100 may optionally have a cap 30 which defines an interior region 31 adapted to encompass the associated head 4 of the associated patient 2. As shown in FIG. 1, the cap 30 may be adapted to be engaged over the associated head 4 and under the harness 70. The cap 30 may have a first side 30A, a second side 30B opposite the first side 30A with respect to the sagittal plane 16, and a set of flaps 32. The set of flaps 32 may have a first flap 34 engaged with the first side of the cap, and a second flap 36 engaged with the second side of the cap. The set of flaps 32 may have a first flap 34 elongated to define a first end 34A of the first flap and a second end 34B the first flap opposite the first end 34A of the first flap. The set of flaps 32 may have a second flap 36 elongated to define a first end 36A of the second flap and a second end 36B the second flap opposite the first end 36A of the second flap. In some embodiments, the second end 34B of the first flap and the second end 36B the second flap are adapted to be selectably engageable with one another to form a chin loop 38 adapted to be secured under a chin 6 of the associated patient 2. In some embodiments, the second end 34B of the first flap and the second end 36B the second flap are adapted to be selectably engageable with one another to form a chin loop 38 by means of an adjustable strap or lockable closure 38A. A lockable closure may be a closure that requires a tool to open. In some non-limiting embodiments the cap 30 further comprises harness fasteners or securing attachment points 39 adapted for operational engagement with the harness 70, In some non limiting embodiments the cap 30 further comprises pad fasteners or securing attachment points 33 adapted for operational engagement with the pads 40.

Also provided is a first method of using an endotracheal tube holder. This latter first method may comprise providing an endotracheal tube 8; providing an associated patient 2 having a head 4. The latter head 4 may have a top 21, a front 23 having a mouth 5, a first cheek 7A, a second cheek 7B, and a chin 6, a back 24 opposite the front 23 with respect to a coronal plane 14, a first side 25, and a second side 26 opposite the first side 25 with respect to a sagittal plane 16 and a transverse plane 12 mutually orthogonal to both the coronal plane 14 and the sagittal plane 16.

This latter first method may comprise providing an endotracheal tube holder of the first embodiment described above or one substantially similar to the endotracheal tube holder of the first embodiment described above. One such acceptable endotracheal tube holder has a flexible and moldable harness adapted to be operatively engaged with the head, the harness having an adjustable transverse band extending in the transverse plane from the front to the back and adapted to be selectably secured around the head: an adjustable coronal band extending in the coronal plane from the first side to the second side and adapted to be selectably secured over the head; a first strap elongated to define a first end of the first strap and a second end of the first strap opposite the first end of the first strap, the first end of the first strap being engaged with the transverse band on the first side; a second strap elongated to define a first end of the second strap and a second end of the second strap opposite the first end of the second strap, the first end of the second strap being engaged with the transverse band on the second side; a set of pads having a first securing pad engaged to the first strap, and a second securing pad engaged to the second strap; and a platform having an elongated rail operationally engaged with and extending between the first securing pad and the second securing pad, a slide operationally and slidably engaged with the rail, and a tube cradle on top of and operationally engaged with the slide, the tube cradle being adapted to selectably engage and hold fast the endotracheal tube.

The first method may further comprise inserting the endotracheal tube into the mouth of the patient; operatively engaging the harness with the head; securing the transverse band around the head; securing the coronal band over the head; and engaging the endotracheal tube with the tube cradle.

The first method above, or other similar methods may further comprise providing a cap which defines an interior region adapted to encompass the head of the associated patient. The cap may be adapted to be engaged over the the head and under the harness, The cap may have a set of flaps wherein the set of flaps have a first flap elongated to define a first end of the first flap and a second end the first flap opposite the first end of the first flap, a second flap elongated to define a first end of the second flap and a second end the second flap opposite the first end of the second flap, wherein the first end of the first flap is engaged with the first side of the cap, wherein the first end of the second flap is engaged with the second side of the cap, and wherein the second end of the first flap and the second end the second flap are adapted to be selectably engageable with one another to form a chin loop adapted to be secured under a chin of the associated patient. In some optional embodiments, this latter method further comprises engaging the cap over the head and under the harness.

Any of the features or attributes of the above described embodiments and variations can be used in combination with any of the other features and attributes of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. An endotracheal tube holder comprising:

a flexible and moldable harness adapted to be operatively engaged with an associated head of an associated patient, the harness having a top, a bottom opposite the top with respect to a transverse plane, a front, a back opposite the front with respect to a coronal plane, a first side, a second side opposite the first side with respect to a sagittal plane, an adjustable transverse band extending in the transverse plane from the front to the back and adapted to be selectably secured around the associated head, an adjustable coronal band extending in the coronal plane from the first side to the second side and adapted to be selectably secured over the associated head, a first strap elongated to define a first end of the first strap and a second end of the first strap opposite the first end of the first strap, the first end of the first strap being engaged with the transverse band on the first side, and a second strap elongated to define a first end of the second strap and a second end of the second strap opposite the first end of the second strap, the first end of the second strap being engaged with the transverse band on the second side, a set of pads having a first securing pad engaged to the first strap, and a second securing pad engaged to the second strap; and a platform having an elongated rail operationally engaged with and extending between the first securing pad and the second securing pad, a slide operationally and slidably engaged with the rail, and a tube cradle on top of and operationally engaged with the slide, the tube cradle being adapted to selectably engage and hold fast an associated endotracheal tube a cap which defines an interior region adapted to encompass the associated head of the associated patient;

the cap being adapted to be engaged over the associated head and under the harness;

the cap having a first side of the cap and a second side of the cap opposite the first side of the cap with respect to a sagittal plane; wherein the cap further comprises fasteners or securing attachment points adapted for operational engagement with the harness;

the cap further having a set of flaps; and wherein the set of flaps have a first flap elongated to define a first end of the first flap and a second end the first flap opposite the first end of the first flap, a second flap elongated to define a first end of the second flap and a second end the second flap opposite the first end of the second flap, wherein the first end of the first flap is engaged with the first side of the cap, wherein the first end of the second flap is engaged with the second side of the cap, and wherein the second end of the first flap and the second end the second flap are adapted to be selectably engageable with one another to form a chin loop adapted to be secured under a chin of the associated patient.

2. The endotracheal tube holder of claim 1, wherein either the first securing pad or the second securing pad further comprises a cushion adapted to protect the associated head of the associated patient.

3. The endotracheal tube holder of claim 2, wherein either the first securing pad or the second securing pad further comprises a band opening adapted to receive a band such as a flexible elastic band, tape or similar material.

4. The endotracheal tube holder of claim 3, wherein the harness is of sufficient area to distribute a holding force over the associated head of the associated patient without harm or discomfort, wherein the holding force sufficient to hold an associated endotracheal tube in place during ordinary patient motion and rotations.

5. A method of using endotracheal tube holder comprising: providing an endotracheal tube;

providing an associated patient having a head, the head having a top, a front having a mouth, a first cheek, a second cheek, and a chin, a back opposite the front with respect to a coronal plane, a first side, and a second side opposite the first side with respect to a sagittal plane and a transverse plane mutually orthogonal to both the coronal plane and the sagittal plane;

providing an endotracheal tube holder having a flexible and moldable harness adapted to be operatively engaged with the head, the harness having an adjustable transverse band extending in the transverse plane from the front to the back and adapted to be selectably secured around the head; an adjustable coronal band extending in the coronal plane from the first side to the second side and adapted to be selectably secured over the head;

a first strap elongated to define a first end of the first strap and a second end of the first strap opposite the first end of the first strap, the first end of the first strap being engaged with the transverse band on the first side;

a second strap elongated to define a first end of the second strap and a second end of the second strap opposite the first end of the second strap, the first end of the second strap being engaged with the transverse band on the second side;

a set of pads having a first securing pad engaged to the first strap, and a second securing pad engaged to the second strap; and a platform having an elongated rail operationally engaged with and extending between the first securing pad and the second securing pad, a slide operationally and slidably engaged with the rail, and a tube cradle on top of and operationally engaged with the slide, the tube cradle being adapted to selectably engage and hold fast the endotracheal tube;

providing a cap which defines an interior region adapted to encompass the head of the associated patient;

the cap being adapted to be engaged over the head and under the harness; the cap further having a set of flaps;

wherein the cap further comprises fasteners or securing attachment points adapted for operational engagement with the harness; and wherein the set of flaps have a first flap elongated to define a first end of the first flap and a second end the first flap opposite the first end of the first flap, a second flap elongated to define a first end of the second flap and a second end the second flap opposite the first end of the second flap, wherein the first end of the first flap is engaged with the first side of the cap, wherein the first end of the second flap is engaged with the second side of the cap, and wherein the second end of the first flap and the second end the second flap are adapted to be selectably engageable with one another to form a chin loop adapted to be secured under a chin of the associated patient;

engaging the cap over the head and under the harness;

inserting the endotracheal tube into the mouth of the patient; operatively engaging the harness with the head;

securing the transverse band around the head; securing the coronal band over the head; and engaging the endotracheal tube with the tube cradle.

6. The method of using endotracheal tube holder of claim 5, wherein either the first securing pad or the second securing pad further comprises a cushion adapted to protect the associated head of the associated patient.

7. The method of using endotracheal tube holder of claim 6, wherein either the first securing pad or the second securing pad further comprises a band opening adapted to receive a band such as a flexible elastic band, tape or similar material.

8. The method of using endotracheal tube holder of claim 7, wherein the harness is of sufficient area to distribute a holding force over the head of the associated patient without harm or discomfort, wherein the holding force sufficient to hold the endotracheal tube in place during ordinary patient motion and rotations.

* * * * *